United States Patent
Troxler

(10) Patent No.: US 6,579,500 B2
(45) Date of Patent: Jun. 17, 2003

(54) APPARATUS AND METHOD FOR DETERMINING WEIGHT LOSS OF A HEATED MATERIAL

(75) Inventor: Robert Ernest Troxler, Raleigh, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

(21) Appl. No.: 10/179,054

(22) Filed: Jun. 25, 2002

(65) Prior Publication Data

US 2002/0164814 A1 Nov. 7, 2002

Related U.S. Application Data

(62) Division of application No. 09/356,184, filed on Jul. 16, 1999, now Pat. No. 6,436,718.
(60) Provisional application No. 60/093,172, filed on Jul. 17, 1998.

(51) Int. Cl.[7] ................................................ G05D 23/00
(52) U.S. Cl. .......................... 422/109; 422/78; 422/307
(58) Field of Search ................................. 436/155, 147; 422/78, 307, 109; 73/863.11

(56) References Cited

U.S. PATENT DOCUMENTS

| | | |
|---|---|---|
| 3,055,206 A | 9/1962 | Watson et al. |
| 3,745,810 A | 7/1973 | McCarter |
| 4,316,384 A | 2/1982 | Pommer et al. |
| 4,459,103 A | 7/1984 | Gieskieng |
| 4,462,474 A * | 7/1984 | Bordeaux et al. .............. 177/48 |
| 5,081,046 A | 1/1992 | Schneider |
| 5,165,792 A | 11/1992 | Crowe et al. |
| 5,279,971 A | 1/1994 | Schneider |
| 5,801,337 A | 9/1998 | Peake |

FOREIGN PATENT DOCUMENTS

| | | | |
|---|---|---|---|
| GB | 2138143 A | * 10/1984 | ........... H03H/11/02 |
| JP | 07260662 A | 10/1995 | |
| JP | 30 73693 B2 | 6/2000 | |

* cited by examiner

*Primary Examiner*—Jill Warden
*Assistant Examiner*—Yelena G. Gakh
(74) *Attorney, Agent, or Firm*—Alston & Bird LLP

(57) ABSTRACT

The present invention provides a method and apparatus for accurately determining weight loss of a sample during heating in a furnace. The method includes the steps of placing a sample in a heated furnace, heating the sample while measurements of sample weight are made, determining rate function from the sample weight measurements, producing a weight loss correction factor using the rate function and using the weight loss correction factor to obtain a corrected weight loss for the sample.

11 Claims, 5 Drawing Sheets

APPARATUS AND METHOD FOR DETERMINING WEIGHT LOSS OF A HEATED MATERIAL

CROSS-REFERENCE TO RELATED APPLICATIONS

This application is a divisional of U.S. application Ser. No. 09/356,184, filed Jul. 16, 1999, now U.S. Pat. No. 6,436,718, which is incorporated herein in its entirety and which claims the benefit of U.S. Provisional Application Serial No. 60/093,172, filed Jul. 17, 1998.

FIELD OF THE INVENTION

This invention is concerned with accurately weighing heated materials, and is especially applicable to a pyrolysis furnace and to the measurement of weight loss in such a furnace.

BACKGROUND OF THE INVENTION

Certain industrial processes require accurate measurement of the weight or mass of a material before it is in a state of thermal equilibrium. In some cases, it is necessary to achieve accuracy on the order of tenths of a gram with samples larger than 3 kg. For example, the construction industry requires the measurement of asphalt content for quality control purposes. Asphalt is a mixture of asphalt binder and aggregate and is used heavily in the construction of roads. The mechanical properties of this mixture depend on many parameters, such as the asphalt binder content by weight and the gradation of the aggregate. In order to measure the quality of these materials, the contractor needs a process to separate the binder from the aggregate.

In the past, there have been several accepted methods to obtain this information. Two such methods involved chemical solvents and nuclear isotopes. The nuclear asphalt content gauge can be used to accurately measure the binder content of asphalt in just a few minutes. Although this method is fast, the drawback is that gradation analysis cannot be obtained. Chemical solvents can give both asphalt content and gradation analysis. However this method is laborious, time consuming, and the waste solvent poses environmental problems.

In recent years, a method of igniting asphalt in order to measure the weight loss due to combustion has become accepted. Although this method is relatively slow as compared to the nuclear techniques, gradation analysis can be obtained as soon as the ash has cooled. With the advent of new technologies in the construction industry, the standards have also become more stringent. Variations in weight loss measurements from lab to production site to construction site, and even furnace manufacturer, must be minimized.

In the conventional industry process, a sample is weighed to the nearest tenth of a gram using an external scale and placed in a basket assembly. The assembly is then placed in a preheated furnace, which is outfitted with an internal scale assembly or load cell. The door is secured, and the weighing process begins. During the first few moments, a tare or beginning weight is measured. During the next few minutes, the asphalt binder begins to burn and the furnace automatically calculates a weight loss relative to the initial weight and calculates the real time asphalt binder content. The entire process may last from 20 to 60 minutes depending on the initial sample weight and design of the furnace.

Since the asphalt is usually mixed at a temperature of about 150° C., and the furnaces are usually preheated to temperatures near 538° C., thermal instabilities exist that make the process of obtaining an accurate initial weight of the asphalt a very challenging endeavor. Typically, the errors incurred are on the order of a few grams, and decrease as the sample temperature approaches the temperature of the furnace. The largest error in the weight loss determined using this method is due to an erroneous tare weight obtained during the first few minutes. Generally, the internal scale in the furnace reports a higher basket assembly weight during the first few minutes in the furnace than one would obtain from an external weighing. This error is the direct result of the temperature differential between the furnace and the sample and basket assembly. Furthermore, the last few minutes in the furnace atmosphere are measured as lighter in weight by the internal scale than one would expect externally. Compared to external scale measurements at ambient temperature, the furnace internal scale overestimates the actual weight loss of the sample.

There have been several attempts to clarify the physics of this effect. In one patent, U.S. Pat. No. 5,279,971 to Schneider, the initial error in tare weight is reported as due to moisture absorbed in the asphalt. However, an asphalt plant mixes these constituents at 150° C. and moisture accounts for a small percent by weight, if any. Even where the sample is dried overnight and all moisture is removed, the same errors occur. The Schneider patent reports that samples should be preheated to 300° C. before placing them in the 550° C. furnace. The Schneider patent states that this reduces the "moisture" error. Actually, the error in tare weight was reduced only because the temperature differential between the sample and furnace was 200° C. as opposed to 400° C.–500° C. with a typical sample removed from the production line.

The temperature error caused by placing a relatively cool sample into an extremely hot oven results in a complicated model involving several external factors, such as air density, air flow, and bombardment of the sample and pan assembly by high energy gas molecules. Furthermore, these factors affect the measurement in different ways according to the properties of the sample, such as mass, thermal capacity, thermal conductance, voids or density, and specific gravity. Thus, there are many different combinations of these variables that perturb the initial measurement. There remains a need in the art for a method of accurately weighing samples in a heated furnace that takes into account the complex effects of thermal instability present during the initial weighing process.

SUMMARY OF THE INVENTION

The present invention provides a method and apparatus for accurately weighing samples in a heated furnace. More particularly, the present invention provides a method and apparatus in which the weight loss of a sample may be accurately determined as the sample is heated in a furnace. In one specific embodiment, the sample is an asphalt binder/aggregate paving mix and the method and apparatus are utilized to accurately measure the asphalt binder content of the paving mix by determining the weight loss resulting from pyrolysis of the asphalt binder. Using the present invention, weight loss values calculated using the internal scales of a furnace are within about 0.05% of the weight loss values calculated with an external scale.

According to the invention, a correction factor is generated which corrects for errors in the measurement of the tare weight of the sample due to external influences and variables such as those noted above. The invention may additionally correct for errors in the end point weight, also due to external influences. A method in accordance with the broad aspects of the invention, includes the steps of placing a sample in a heated furnace, heating the sample while measurements of sample weight are made, determining a rate function from the sample measurements, producing a weight loss correction factor using the rate function, and using the weight loss correction factor to obtain a corrected weight loss for the sample.

In another aspect, the method includes the steps of placing a combustible sample in a heated furnace, heating the sample while measurements of the weight of the sample are made, determining a weight loss rate function from the sample weight measurements, determining the approximate time at which the onset of sample combustion occurs, producing a weight loss correction factor using the time of combustion onset and the weight loss rate function, and using the weight loss correction factor to obtain a corrected weight loss for the sample.

The weight loss rate function may be suitably determined from the sample weight measurements using regression analysis, such as least squares regression analysis, or other known techniques. During the initial heating of the sample prior to combustion, the weight loss rate may be suitably modeled by a linear function, although other functions could be employed. The time at which the onset of sample combustion occurs can be ascertained in a number of ways. In one embodiment or aspect, combustion onset may be determined by observing the time at which the weight loss rate ceases to be linear, or departs from linear by some threshold amount. In another embodiment or aspect, combustion onset may be determined by monitoring the rate of change in sample temperature or combustion chamber temperature and determining therefrom the projected time at which the sample will reach a known combustion temperature for the particular sample or some other selected temperature. Still another approach involves monitoring the rate of change in sample temperature or combustion chamber temperature and determining the time at which the temperature change rate ceases to be linear, or departs from linear by some threshold amount. Instead of relying upon combustion onset time, it is possible to use other values, such as combustion onset time less 10% or even a fixed time interval. The appropriate method of determining the combustion onset time or other value may depend, in part, on the design of the furnace.

The present invention also provides an apparatus for determining weight loss of a sample, comprising a furnace, a scale mounted within the furnace for measuring sample weight, a data store operatively connected to said scale for storing sample weight measurements, and a weight loss correction factor generator for generating a weight loss correction factor using the sample weight measurements in the data store. The apparatus may also include means for generating a corrected weight loss measurement using a final sample weight measurement from the data store and the weight loss correction factor.

Preferably, the weight loss correction factor generator comprises means for determining a weight loss rate function from the sample weight measurements in the data store, means for determining the approximate time of combustion onset, and means for generating a weight loss correction factor using the time of combustion onset and the weight loss rate function.

Additional features and aspects of the invention will become apparent from the detailed description which follows and from the accompanying drawings, which are intended to be illustrative of the invention, but not restrictive as to the scope and breadth of the invention.

BRIEF DESCRIPTION OF THE DRAWINGS

Figure 1:
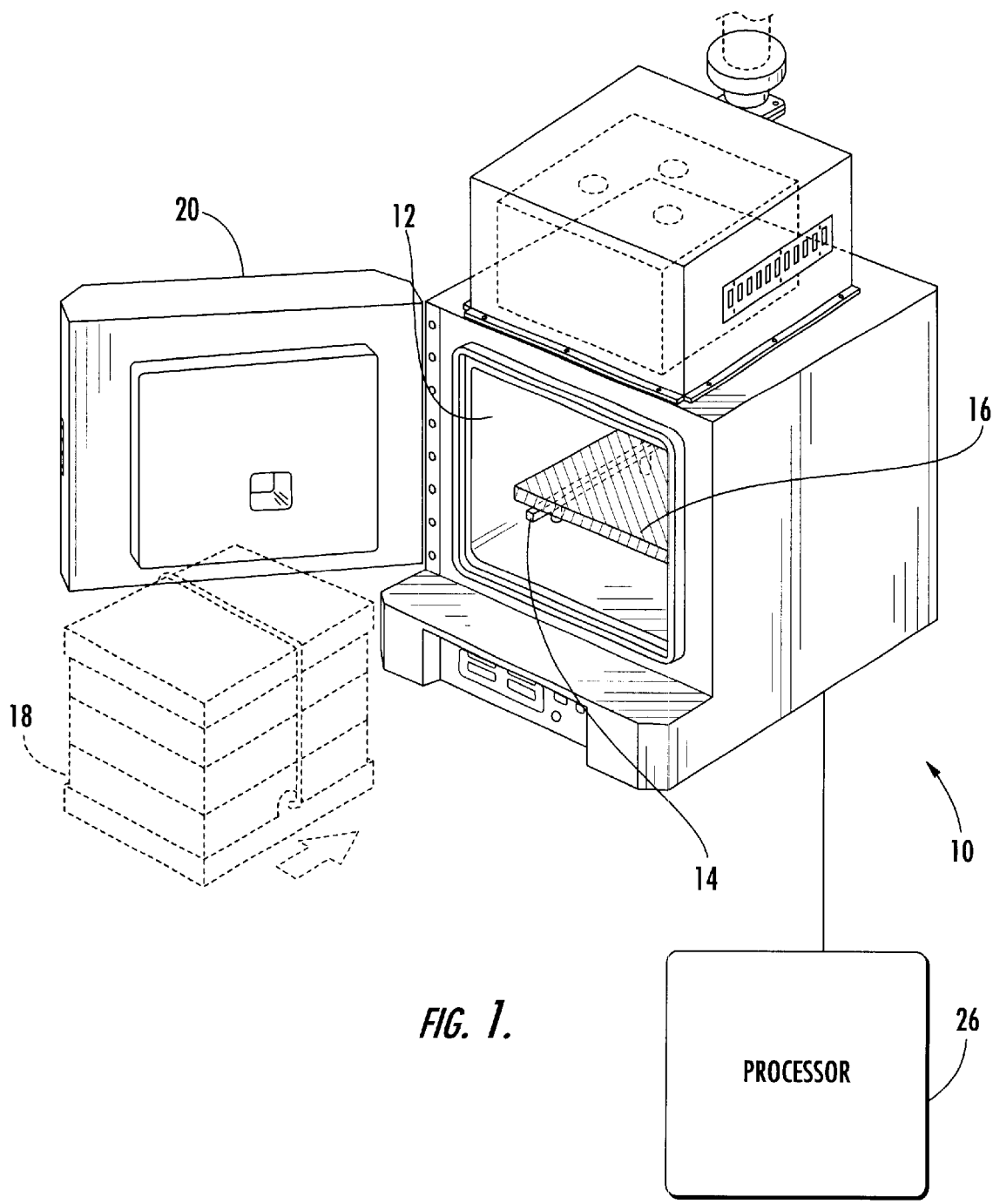
Figure 2:
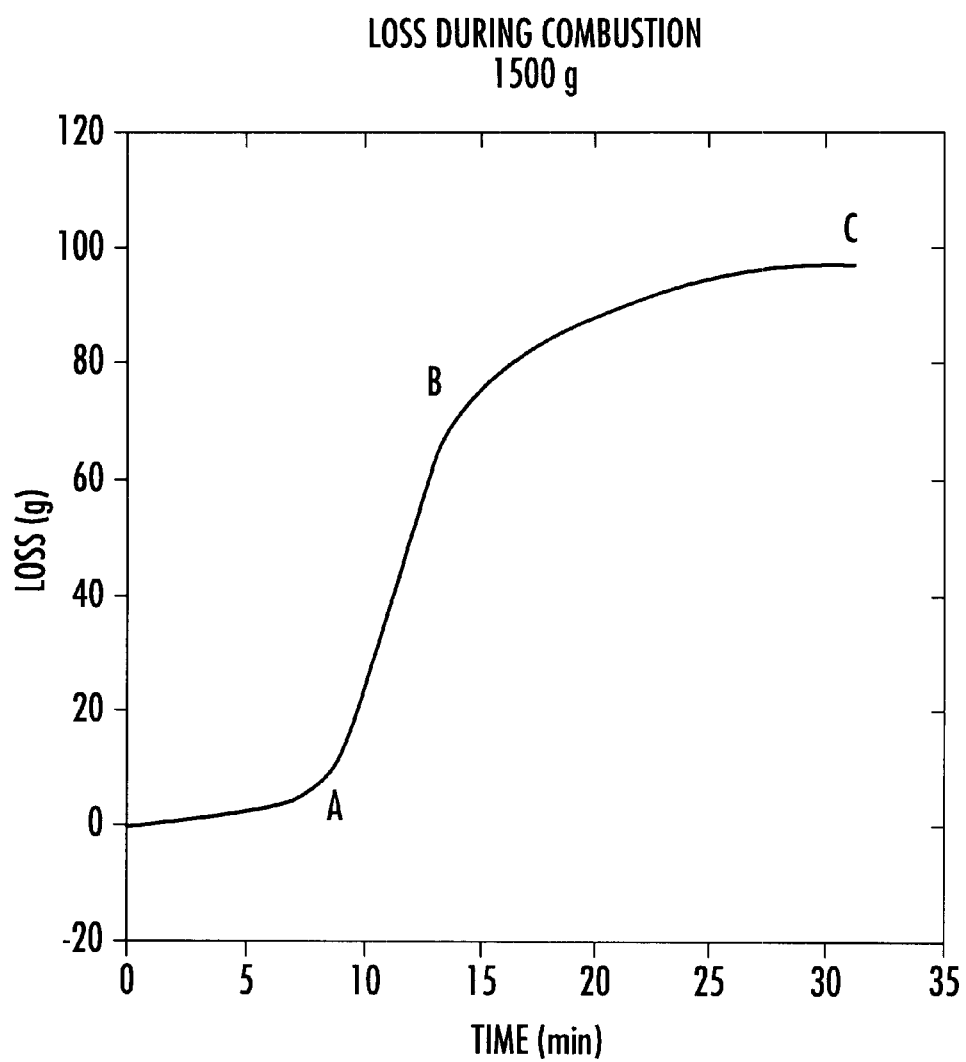
Figure 3:
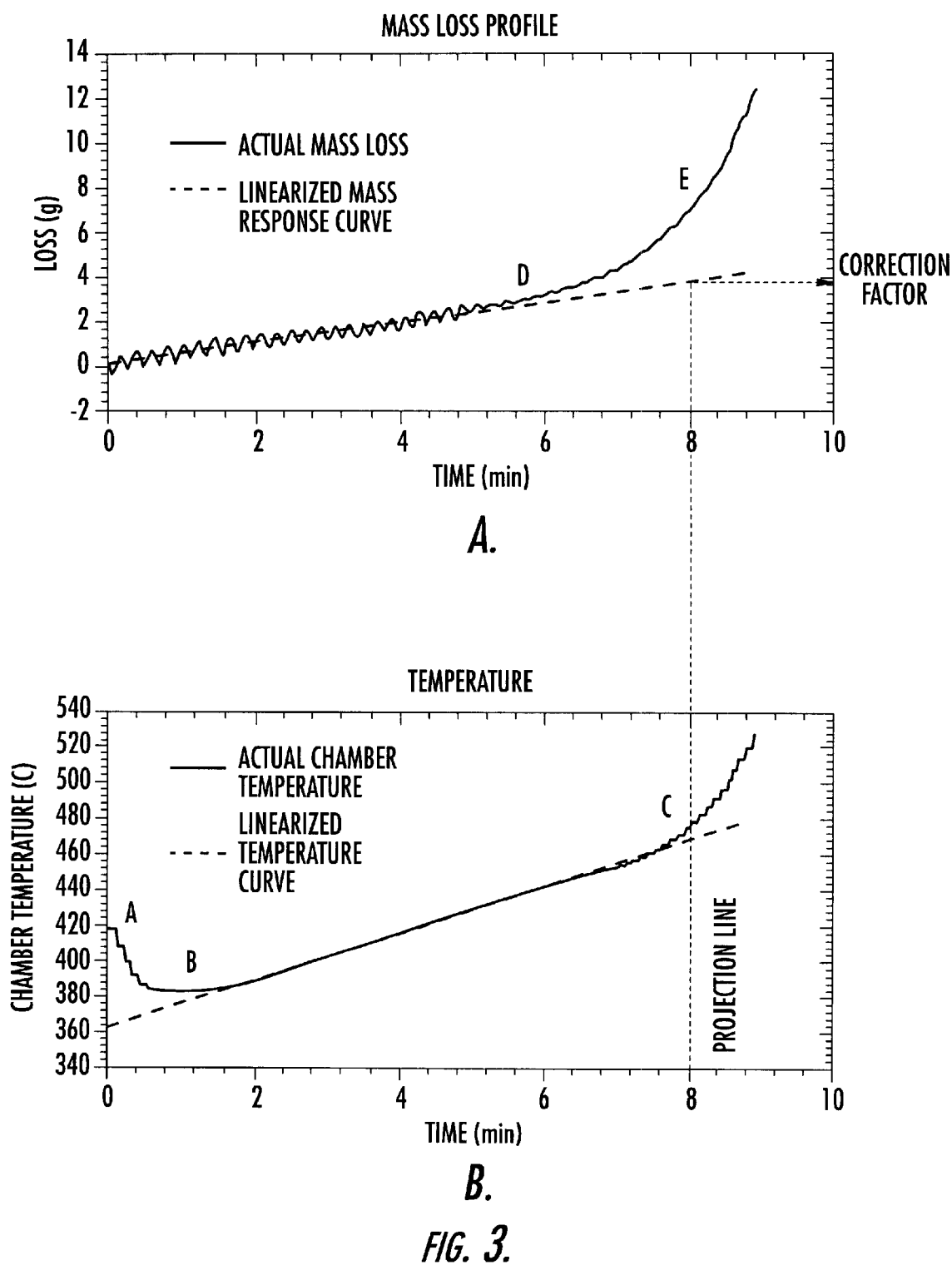
Figure 4:
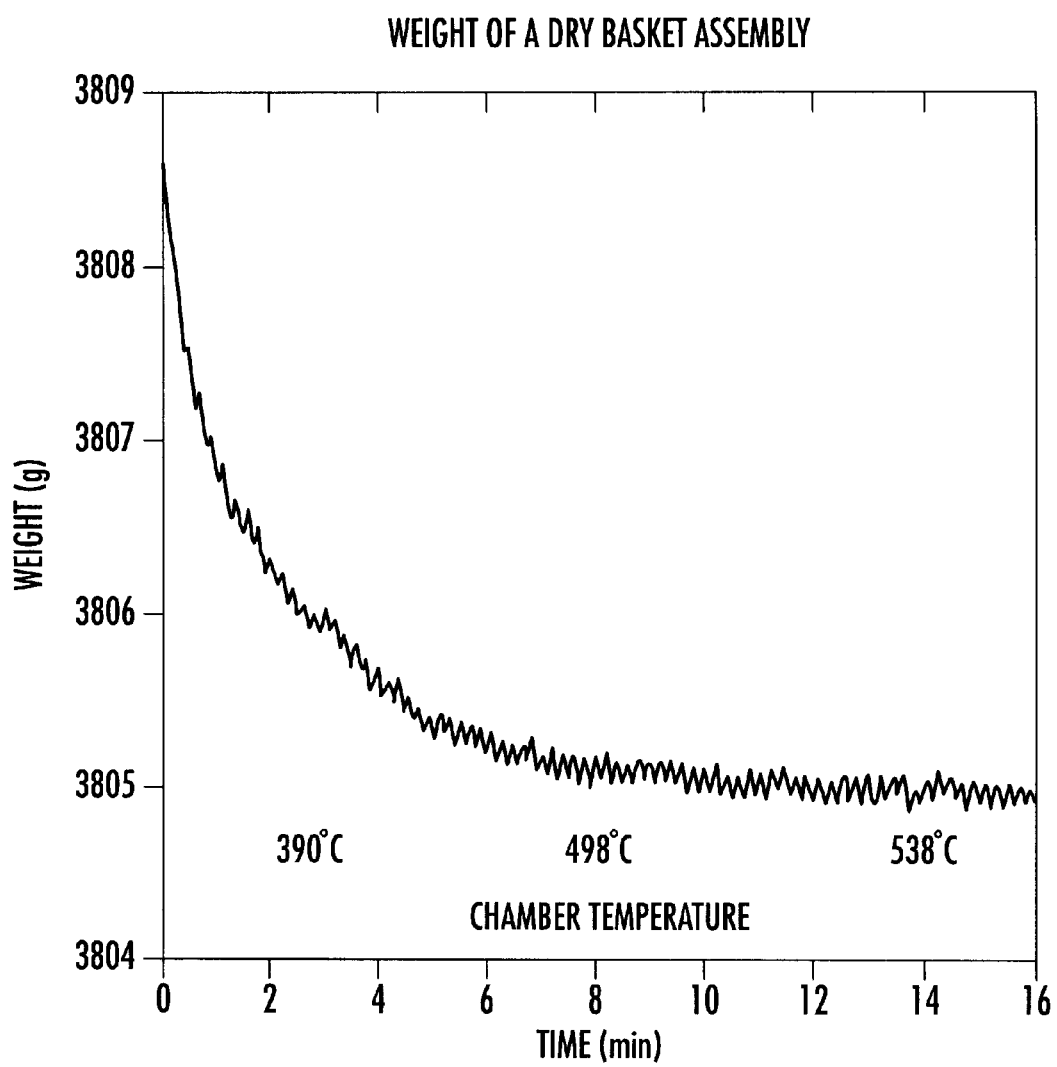
Figure 5:
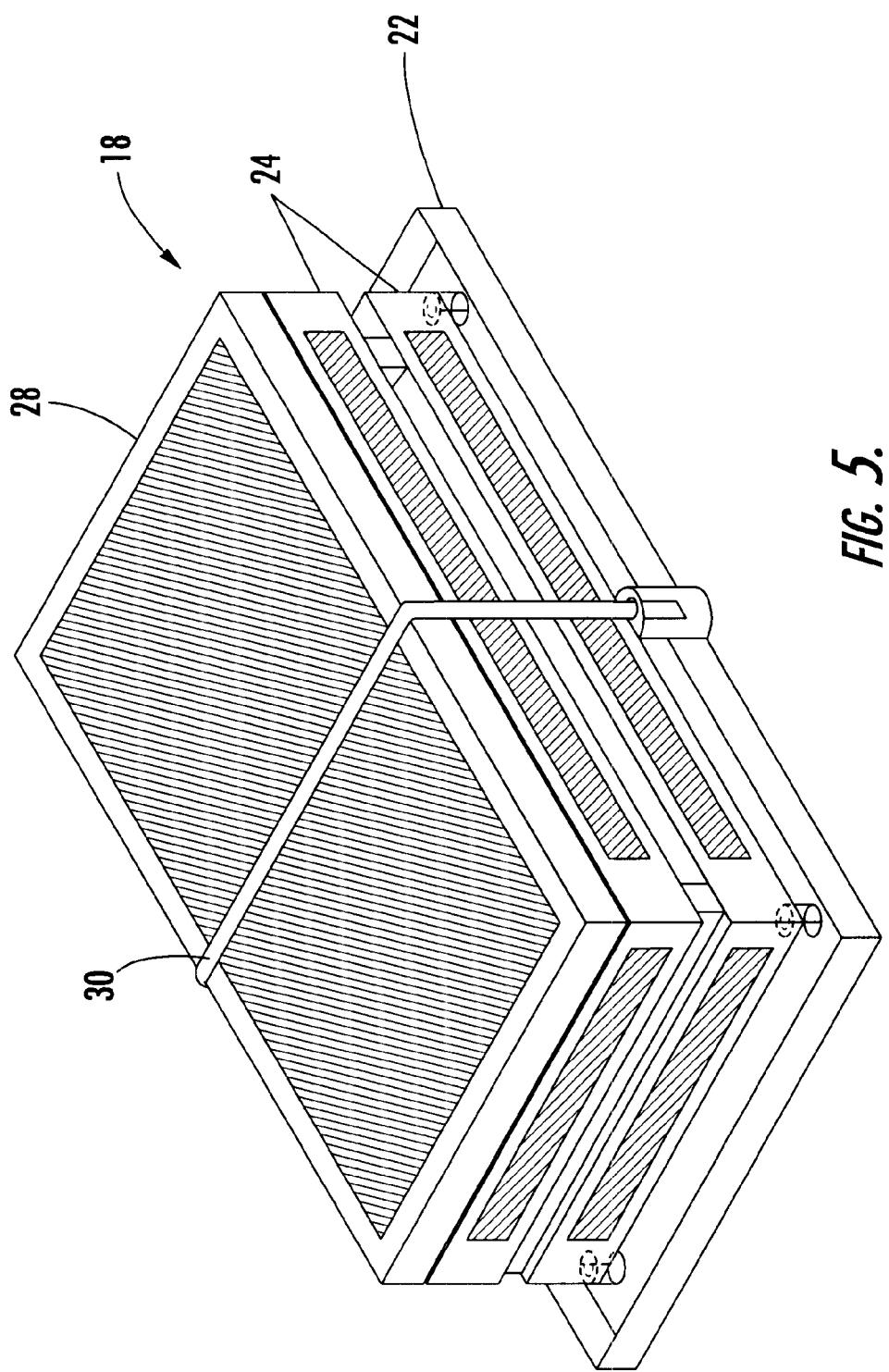

Having thus described the invention in general terms, reference will now be made to the accompanying drawings, which are not necessarily drawn to scale, and wherein:

FIG. 1 illustrates a preferred design of an analytical furnace useful in the present invention;

FIG. 2 illustrates a typical burn cycle for a 1,500 gram sample;

FIG. 3 illustrates the mass or weight loss profile and temperature profile of the first ten minutes of a typical burn cycle;

FIG. 4 illustrates the effect of heating on the weight of an empty pan assembly; and FIG. 5 illustrates a preferred design of a pan assembly useful in the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

FIG. 1 illustrates an analytical furnace 10 with a combustion chamber 12 and a door 20 that provides access to the combustion chamber. The furnace 10 further includes a sample support 14 that is operatively connected to an internal scale assembly (not shown) that measures the weight of the sample during the combustion cycle. In one embodiment, the support 14 comprises a pair of rails positioned to receive a sample. The internal scale may be any known weighing device in the art, such as a load cell.

A heat transfer plate 16 may be placed above the sample support 14. The sample, such as asphalt, is placed in a sample pan assembly 18 and placed in the combustion chamber 12 such that the pan assembly rests on the plate 16 during heating. A temperature sensor (not shown), such as a thermocouple, is strategically located near the sample to measure chamber or sample temperature.

The plate 16 increases the transfer of heat into the sample and aids in preheating the air as it enters the chamber 12 through holes below the plate. To this end, the plate 16 is preferably made of a material having high thermal heat capacity and good heat conductivity. Particularly suitable are materials such as silicon carbide, aluminum oxide and some metals. Quick transfer of heat into the pan assembly 18 assists in reducing the settling time and duration of thermal instability.

Advantageously, a processor 26 is operatively connected to the furnace 10. The processor 26 may be any combination of computer hardware and software capable of performing calculations arid manipulating data as needed to practice the present invention. Preferably, the processor 26 includes one or more data stores for storing data such as weight and temperature readings. Additionally, the processor preferably includes a digital filter for filtering data measurements, such as weight and/or temperature measurements, to dampen or reduce oscillations and noise caused by the mechanical vibrations of a thermally expanding system. The digital filter smoothes the response of the weight and/or temperature data. The digital filter could be as simple as an N pole low pass Butterworth-type filter, or even an adaptive filter as known to one skilled in the art.

Typically, the furnace 10 is utilized to measure the weight of a combustible portion of a sample by measuring the weight of the sample before and after combustion of the combustible portion of the sample. A commercially available furnace suitable for use with the present invention is Model 4155B available from Troxler Electronic Laboratories. As used herein, combustion refers generally to the boiling, evaporation, thermal degradation and thermal decomposition of the combustible portion of a sample.

FIG. 2 illustrates a typical burn cycle of a combustible sample with time as the abscissa and weight loss in grams on the ordinate. The burn cycle shows the weight loss that occurs during a combustion cycle, from the time the sample is placed in the furnace until combustion of the combustible portion of the sample is complete. At t-0, the sample is loaded into the chamber and the process begins. Point A indicates the beginning of the burn cycle. Between t=0 and point A the system marks a beginning point commonly referred to as the tare. Point B marks the end of the flame, and point C indicates the end of the cycle, as determined by a slope of less than 0.1 g per minute. In an automated data collection system, the asphalt content by weight is calculated using the difference between the weight loss of paint C and the tare.

FIG. 3 shows the expanded view of the burn cycle concentrating on the first 10 minutes. The material weight loss is shown in FIG. 3A while the chamber temperature is illustrated in FIG. 3B. When the sample is first loaded into the chamber, the chamber temperature begins to drop. This is evident from the response between points A and B. The temperature then increases in a linear fashion to point C where a positive identification of the burn is evident by the deviation from the linear response.

As shown in FIG. 3A, at t=0, the weight loss increases in a linear fashion up to point D. Between points D and E the function describing loss deviates from a linear relationship. The ripple in the weight curve is due to oscillations in the pan assembly 18. During the initial heating of this assembly 18, the pans may warp and begin to rock on the platform at a frequency determined by the rocking moment and mass of this assembly and the sample.

It has been hypothesized that all the loss from t=0 to point E of FIG. 3A was due to moisture evaporation from the sample. However, FIG. 4 shows a similar weight loss response even with an empty pan assembly 18. Note that FIG. 4 is a graph of total weight rather than weight loss. This indicates that the weight loss during the first few minutes is a phenomenon linked with temperature instabilities and not moisture. The moisture error theory lead to the practice of reading the weight loss directly off the curve of FIG. 3A at point E, as taught by U.S. Pat. No. 5,279,971 to Schneider. Unfortunately, the weight loss obtained by interpreting the correction factor exclusively by the weight indicated by E also contains the boiling, evaporation and thermal degradation of the asphalt material. Thus, the Schneider method actually underestimates the weight of the asphalt binder by incorporating some of the weight lost due to combustion of the binder in the correction factor.

One of the largest effects pertaining to an inaccurate tare is due to the difference in air densities and void content of the asphalt sample. During the initial linear portion of the weight loss curve, the relatively cold asphalt is out-gassing and becomes lighter. The bombardment of the pan assembly 18 by energetic gas molecules creates a transfer of momentum or force, which also decreases as thermal equilibrium approaches. Furthermore, during this period the airflow and turbulence created in the combustion chamber 12 begins to settle. When this process is near completion, evaporation of the petroleum-based bitumen of the asphalt begins, as indicated by point D of FIG. 3A. This is the beginning of the nonlinear response of the weight loss curve. However, even though the outgassing has decreased by point D, it is not complete, but merely accompanied by evaporation up until the point of combustion located at point E.

As previously stated, a problem arises when the tare is obtained before thermal stability has been achieved. Unfortunately, with a combustible sample, thermal stability is not achieved until after point B in FIG. 2. Hence a weight loss correction factor, typically measured in grams, is necessary to obtain the proper beginning weight.

The present invention provides a method of accurately determining the weight loss of a sample during heating, wherein the method includes using a weight loss correction factor to obtain a corrected weight loss for the sample. The method includes placing a sample, such as a combustible sample, in a heated furnace and heating the sample while measurements of sample weight are made. The sample weight measurements are used to determine a rate function. The rate function, in turn, is used to produce a weight loss correction factor. Thereafter, the weight loss correction factor may be used to obtain the corrected weight loss of the sample.

The sample weight measurements define a weight loss curve, such as illustrated in FIG. 3A, wherein the curve includes an initial substantially linear portion and a subsequent non-linear portion. Preferably, the rate function is a weight loss rate function comprising a function corresponding to the substantially linear portion of the weight loss curve. The weight loss rate function may be determined by applying a regression analysis, such as a least squares regression analysis, to the sample weight measurements. In a preferred embodiment, the weight loss rate function comprises a linear function corresponding to the substantially linear portion of the weight loss curve.

Once the rate function is determined, the initial substantially linear portion of the weight loss curve may be linearly extrapolated beyond the linear portion of the weight loss curve. Since it is believed the linear portion of the weight loss curve is mainly attributable to weight measurement errors caused by thermal instabilities as discussed above, extrapolation of the linear portion of the weight loss curve to the approximate point of combustion will provide a weight loss correction factor that will negate the effect of thermal instability on the measurement of weight loss of the sample. The remaining weight loss (occurring after the approximate onset of combustion) should be attributable to combustion of the combustible portion of the sample, such as asphalt binder.

Thus, in a preferred embodiment of the invention, the onset of combustion or approximate onset of combustion is determined in order to ascertain the point at which changes in weight are no longer attributable to thermal instabilities present in the furnace. As shown in FIG. 3A, once this time is known, the weight loss correction factor may be calculated by extrapolating the rate function to that time.

For example, in one embodiment, when the approximate combustion time has been determined, the calculated time is inserted into the weight loss rate function to determine the weight loss correction factor. Where a linear function is used, the time is multiplied by the slope of the linear equation derived from the substantially linear portion of the weight loss curve, and the intercept of the linear equation is added to this result to obtain the weight loss correction factor. Notice that this calculated value is much less than the measured weight loss at this point in time, as the measured weight loss has partially incorporated the combustion of the asphalt binder, or other combustible portion, of the sample.

The approximate onset of combustion may be determined in a number of ways. For example, as shown in FIG. 3A, the approximate onset of combustion results in a departure of the weight loss curve from a linear response. Thus, the onset of combustion may be determined by determining the time at which the weight loss rate departs from a linear function by a threshold amount. The threshold amount may vary from zero to any suitable amount, such as about three grams. In other words, the approximate point of combustion may be determined as the time at which the actual measured weight of the sample deviates from the extrapolated weight calculated using the rate function by a threshold amount.

Similarly, the approximate onset of combustion may be determined using the temperature profile as shown in FIG. 3B. As shown, the chamber temperature or sample temperature departs from a linear function at the approximate point of combustion. Thus, the onset of combustion may be determined by monitoring the rate of change in sample or combustion chamber temperature and determining the time at which the rate of change of the monitored temperature departs from a linear function by a threshold amount. For example, a rate function for the substantially linear portion of the temperature curve may be calculated and extrapolated. The actual temperature of the sample or chamber may be compared to the extrapolated temperature calculated using the rate function and the onset of combustion may be determined as the time at which the two values diverge by a threshold amount, such as about 10° C.

Alternatively, the onset of combustion may be determined as the time at which the sample temperature or combustion chamber temperature reaches a predetermined temperature. Since asphalt typically ignites at a temperature of about 460° C., the onset of combustion may be approximated by simply determining the time at which 460° C. is reached in the combustion chamber and using that time, and the rate function discussed above, to calculate the weight loss correction factor. Further, repeated experimentation with samples of a known initial weight using the same furnace would enable the user to determine the appropriate onset of combustion time without reference to temperature data. For example, if several 1500 gram samples are burned in a particular furnace, the user could estimate the time to combustion for that sample size in that furnace type.

Once the weight loss correction factor is calculated, the final corrected weight loss of the sample may be calculated by subtracting, or otherwise applying, the weight loss correction factor from the final measured weight loss of the sample. In this manner, the approximate weight loss attributable to thermal instability or other external factors is removed from the final weight loss calculation, resulting in greater accuracy.

The integrity of this method is associated with the slope of the weight curve. In practice, small masses reach equilibrium at a faster rate than larger masses. Likewise, different installations and systems will achieve thermal equilibrium at differing rates. In this case, the response of the sample is related to the thermal capacity of the furnace, the sample, and airflow of the installation. However, these parameters are naturally accounted for through the slopes of the linearized weight and temperature curves.

As explained above, a linear function is believed to adequately model the weight loss due to thermal instability. However, other functions known in the art could be used for the rate function. For example, an exponential function, such as Equation 1, is believed to accurately model weight loss of a sample due to thermal instability.

$$\text{Loss} = A*EXP(Bt) + C \qquad \text{Equation 1}$$

Equation 1 could be used to determine a weight loss correction factor without determining onset of combustion where a single type or model of furnace is utilized. If all furnaces that will utilize the rate function are of the same type, so that characteristics such as heat-up time, airflow and physical size of the chamber and pan assembly are the same, a statistical sampling of the furnaces can be used to determine the exponential coefficient, B. Likewise, the manufacturer of a particular furnace type could calculate the B coefficient for each individual furnace. For example, a non-combustible material could be inserted in the furnace and several weight loss versus time measurements could be taken in order to determine the B coefficient.

Once the B coefficient is known for the particular furnace, only two weight loss measurements are required in order to solve Equation 1 for the remaining two constants, A and C. Once A and C are known, the weight loss correction factor may be calculated as the limit of Equation 1 as t goes to infinity. Thus, using this method, the weight loss correction factor is equal to the C constant.

When the pan assembly 18 is first placed into the chamber 12, it undergoes rapid expansion, which results in disproportionate instabilities. Hence, a delay is preferably incorporated into the method of the present invention to ignore this period. For example, a delay of about 20 to about 40 seconds may occur before sample weight measurements are begun. The delay may be incorporated into the furnace 10 using, for example, a delay timer incorporated into the processor 26. Following the delay, sample weight measurements are begun.

Preferably, the sample or combustion chamber temperature is also monitored to determine when the minimum occurs. This allows further settling time to the pan assembly 18, and more importantly, generally signals the beginning of the linear range of the chamber or sample temperature curve. Preferably, temperature data collection begins after the chamber temperature reaches the minimum. Typically, the chamber temperature reaches the minimum value about two minutes after the sample is placed in the furnace, but the time may vary depending on furnace type. Once the temperature minimum occurs, both weight and temperature data are collected and preferably continue to be stored until the weight loss curve begins to become nonlinear. Typically, for small samples, data collection can occur up to about 4 or 5 minutes, while larger masses remain linear for as much as 6 to 8 minutes. Preferably, the weight data is collected for at least about two minutes to ensure that sufficient data is taken to accurately determine the weight loss rate function. One way to detect when the weight curve becomes nonlinear is to calculate the residuals between the actual data and the corresponding linear curve-fitted data. When the residuals become greater than some predetermined value, then data collection is ceased. It is also possible that each curve (T and weight) are individually analyzed, as the temperature response remains linear long after the weight has deviated.

The weight and temperature measurements discussed above, and calculations utilizing those measurements, may be stored and manipulated manually or using processor 26. Preferably, the temperature and weight data are fed into processor 26 and the processor performs all calculations and curve-fitting functions.

A preferred design of the pan assembly 18 is shown in FIG. 5. During the data collection period, rapid thermal expansion takes place in the pan assembly 18. This expansion causes oscillations and reduces the signal to noise ratio of the weight measurement. To reduce these effects, a preferred design of the pan assembly 18 incorporates a material with a low thermal expansion coefficient, such as stainless steel. The pan assembly 18 is also perforated to allow oxygen to flow into the sample, and the lower catch pan 22 has a cross break to add mechanical strength and rigidity. The air gaps between the sample pans 24 and catch pan 22 aid in oxidizing the asphalt while decreasing the total burn time. Preferably, the pan assembly 18 further includes a perforated top cover 28 and a bail strap 30 to hold the assembly in place.

The present invention provides a method of measuring weight loss in an analytical furnace capable of consistently measuring weight loss regardless of the furnace type, thermal capacity of the furnace, thermal conductance and capacity of the sample, weight and void ratio of the sample, installation variances, the temperature difference between the sample and furnace and volume of the basket assembly.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for determining weight loss of a sample, comprising:

a furnace, said furnace comprising a combustion chamber and a door providing access to said combustion chamber;

a scale mounted within said furnace for measuring sample weight;

a data store operatively connected to said scale for storing sample weight measurements;

means for determining a weight loss rate function from the sample weight measurements in said data store;

means for determining the approximate time at which the onset of sample combustion occurs; and means for generating a weight loss correction factor using the approximate time of combustion onset and the weight loss rate function.

2. An apparatus according to claim 1, further comprising:

a temperature sensor mounted within said combustion chamber, said temperature sensor operatively positioned to measure sample or combustion chamber temperature; and a second data store operatively connected to said temperature sensor for storing temperature measurements.

3. An apparatus according to claim 1, further comprising means for generating a corrected weight loss measurement using a final sample weight measurement from said data store and said weight loss correction factor.

4. An apparatus according to claim 1, wherein said means for determining the combustion onset time comprises means for determining the time at which the weight loss of the sample departs from a linear function by a threshold amount using the weight measurements in said data store.

5. An apparatus according to claim 1, wherein said means for determining the combustion onset time comprises:

a temperature sensor mounted within said combustion chamber, said temperature sensor operatively positioned to measure sample or combustion chamber temperature;

a second data store operatively connected to said temperature sensor for storing temperature measurements; and means for determining the time at which the rate of change in the stored temperature measurements departs from a linear function by a threshold amount using the measurements in said second data store.

6. An apparatus according to claim 1, wherein said means for determining the combustion onset time comprises:

a temperature sensor mounted within said combustion chamber, said temperature sensor operatively positioned to measure sample or combustion chamber temperature;

a second data store operatively connected to said temperature sensor for storing temperature measurements; and means for determining the time at which the measured temperature reaches a predetermined temperature using the measurements in said second data store.

7. An apparatus according to claim 1, further comprising a digital filter operatively connected to said data store for filtering sample weight measurements.

8. An apparatus according to claim 7, wherein said digital filter comprises a low pass filter.

9. An apparatus according to claim 1, further comprising a delay timer operatively connected to said scale to delay the measurement of sample weight for a predetermined amount of time.

10. An apparatus according to claim 1, further comprising a plate overlying said scale.

11. An apparatus according to claim 1, further comprising a pan assembly operatively positioned for weighing on said scale.

* * * * *